United States Patent [19]

Norton

[11] 3,935,238

[45] Jan. 27, 1976

[54] PREPARATION OF PHTHALATE ESTERS

[75] Inventor: Richard V. Norton, Wilmington, Del.

[73] Assignee: Sun Research and Development Co., St. Davids, Pa.

[22] Filed: Jan. 15, 1973

[21] Appl. No.: 323,477

[52] U.S. Cl. ......... 260/475 R; 260/469; 260/471 R; 260/473 R; 260/473 F; 260/475 FR; 260/476 R
[51] Int. Cl.² ................. C07C 69/80; C07C 69/82
[58] Field of Search .......... 260/475 R, 476 R, 469, 260/473 R, 473 F, 471 R

[56] References Cited
UNITED STATES PATENTS

| | | | |
|---|---|---|---|
| 2,565,487 | 8/1951 | Filachione et al. | 260/476 R |
| 2,926,189 | 2/1960 | Hadley et al. | 260/475 P |
| 3,123,632 | 3/1964 | Katzschmann | 260/475 R |
| 3,320,303 | 5/1967 | Schenk et al. | 260/475 R |
| 3,377,376 | 4/1968 | Gainer et al. | 260/475 R |

*Primary Examiner*—Robert Gerstl
*Assistant Examiner*—E. Jane Skelly
*Attorney, Agent, or Firm*—J. Edward Hess; Donald R. Johnson; Paul Lipsitz

[57] ABSTRACT

A process for the preparation of a lower alkyl ester of a phthalic acid by contacting an ammonium salt of an aromatic carboxylic acid with vapors of a lower alkanol at a temperature between about 230°C and about 300°C in the presence of an alkaline esterification catalyst.

11 Claims, No Drawings

PREPARATION OF PHTHALATE ESTERS

Esters of aromatic carboxylic acids such as phthalic acids are important chemicals of commerce which are useful as plasticizers, as films and fiber intermediates, and the like. It is known to make such esters by conventional esterification processes from the carboxylic acid and the alcohol using various techniques. Thus, U.S. Pat. No. 3,364,251 (Benning et al, issued Jan. 16, 1968) discloses reacting the acid in the solid state with the alcohol in a fluidized bed at 280° to 300°C. U.S Pat. No. 3,377,376 (Gainer et al, issued Apr. 9, 1968) discloses a vapor phase reaction between an aromatic dicarboxylic acid (e.g., terephthalic acid) and an alcohol at 600° to 760°F in the presence of a solid esterification catalyst impregnated with an alkali metal oxide. Also of interest is U.S. Pat. No. 3,320,303 (Schenk et al, issued May 16, 1967) which describes theh preparation of terephthalic acid esters by reaction of a monoalkali metal salt of terephthalic acid (derived from the dialkali metal terephthalate) with methanol in a liquid phase reaction at 80° to 350°C and in the presence of an esterification catalyst.

All of the above processes require the use of the free phthalic acid, either alone or as an intermediate to alkali metal salt used for conversion to the ester. Thus, such processes are useful where the carboxylic acid is made by a process which yields the acid directly, as for example, by the liquid phase cobalt-catalyzed oxidation of an alkyl-aromatic hydrocarbon (e.g., xylene) such as disclosed in U.S. Pat. No. 2,853,514, 3,036,122, and by Henkel technology where alkali metal carboxylates are rearranged to give a free acid product. There are available, however, vapor phase ammoxidation processes where aromatic carboxylic acids may be made by hydrolysis of the corresponding nitriles obtained by ammoxidation (see U.S. Pat. No. 2,833,807, Farkas et al, issued May 6, 1958 and U.S. Pat. No. 2,838,558, Hadley et al, issued June 10, 1958). In such processes, the nitrile hydrolysis yields mono- and diammonium salts of the acids, the acids subsequently being obtained therefrom. It is clear that a significant advance in the art would be achieved if the carboxylate esters could be obtained directly from the ammonium carboxylates as this would completely eliminate the need to convert to free acids the ammonium salts obtained by hydrolyzing the corresponding nitriles from ammoxidation reactions. This invention provides this advance.

In accord with the invention, lower alkyl esters of aromatic carboxylic acids are prepared by contacting an ammonium salt of an aromatic carboxylic acid with vapors of a lower alkanol at a temperature between about 230° and about 300°C in the presence of an alkaline esterification catalyst.

The esters made by the process of the invention will include those derived, preferably, from carboxylic acid salts of the benzene and naphthalene series. The process is operable with mono- and polyammonium carboxylate salts and will include the ammonium salts of benzoic, isophthalic, terephthalic, naphthalene, mono- and polycarboxylic acids and the like. It will be understood that the aromatic ring may also be substituted with inert groups such as halogen, alkyl, aryl, nitro, alkoxy and the like. It is also to be understood that if two carboxylic acid salt groups are present in the aromatic reactant which are ortho to each other there is a tendency for imide formation to occur and ester yield to be low. Other ammonium carboxylate groups in the reactant will be efficiently converted to the ester, but in the case of the phthalic acid and 1,8-naphthalene carboxylic acid salts, imide formation rather than ester formation will predominate. Thus, the process is preferably carried out with aromatic acid ammonium salts which are devoid of adjacent (ortho or peri) carboxylic acid groups. The alkyl of the ester radical will be lower alkyl as derived from the reactant alcohol; e.g., methanol, ethanol, n- and iso-propanols, the butanols, and the like. Preferably, the process will be carried out with the mono- and diammonium salts of iso- and terephthalic acid, the alcohol being methanol or ethanol.

The catalyst used in the process of the invention may be any of the numerous and well known alkaline esterification catalysts such as oxides of silicon, titanium, aluminum, zirconium, thorium, and the like which have been treated with an alkali metal hydroxide (e.g., NaOH, KOH, etc.) and heated so as to contain at least about 0.2% by weight of the alkali metal oxide. Such catalysts and their method of preparation are well known (see U.S. Pat. No. 3,377,376).

In carrying out the process of the invention the ammonium phthalate salts are contacted with vapors of the alkanol and passed over a fixed or fluidized bed of the catalyst. The process may be carried out by fluidizing the catalyst and salt with the ammonia vapors, or the mixture of alkanol and salt simply passed through a column of the catalyst. After issuing from the reactor, the ester products are separated by conventional methods using filters, cyclones, distillation techniques and the like as required by the physical properties of the product. It will be understood that where the diester is the desired product, any monoester that remains in the product may be separated and recycled for further reaction of the remaining ammonium salt group with alkanol.

As pointed out above, the process of the invention is of particular value with nitrile hydrolysates. As is well known, hydrolysis of phthalonitriles yields the ammonium salts of the corresponding acids, but also present are incompletely hydrolyzed by-products such as phthalamates, ammonium salts of mononitrile compounds, etc. It is a particular advantage of the process that such hydrolysates may be taken directly into the reactor with the alkanol whereby completion of the hydrolysis to the ammonium salts is made to occur in-situ by introducing water vapor to the system and conversion of the ammonium salts to ester will also be achieved. Thus, tedious isolation procedures may be avoided.

In order to further illustrate the invention, the following examples are given:

EXAMPLES 1–8

In the following examples, vaporized diammonium or monoammonium terephthalate is reacted with vaporized alcohols at the mole ratios and temperatures indicated. As a control, terephthalic acid is used under identical conditions. Basic silica gel prepared by evaporating an ethanolic solution of 1 part by weight of KOH on 100 parts of $SiO_2$ is used as the catalyst.

TABLE I

|  | Example | | | | | | | |
|---|---|---|---|---|---|---|---|---|
|  | I | II | III | IV | V | VI | VII | VIII |
| DAT* (moles) | 0.3 | 0.3 | 0.0 | 0.0 | 0.3 | 0.2 | 0.1 | (0.3 TPA) |
| MAT⁺ (moles) | 0.0 | 0.0 | 0.3 | 0.3 | 0.0 | 0.0 | 0.2 | 0.0 |
| $CH_3OH$ (moles) | 1.2 | 4.8 | 1.2 | 4.8 | 4.8 | 0.0 | 4.8 | 4.8 |
| EtOH (moles) | 0.0 | 0.0 | 0.0 | 0.0 | 0.0 | 1.6 | 0.0 | 0.0 |
| Temp (°C) | 250 | 255 | 250 | 253 | 290 | 240 | 255 | 255 |
| Contact Time (sec) | 1.7 | 1.7 | 1.6 | 1.8 | 1.3 | 1.5 | 1.7 | 1.7 |
| Ester Yield | 54 | 71 | 46 | 55 | 67 | 68 | 63 | 37 |

*diammonium terephthalate
⁺monoammonium terephthalate

Comparison of I with II indicates that the higher alcohol to salt ratio gives higher ester yield. Comparison of III with IV shows a similar increase in yield. Comparison of I with III and comparison of II with IV indicates that the ammonia released during esterification promotes the catalytic activity of the silica gel as shown by the higher dimethyl terephthalate yield. Examples V and VI give an indication of the operable temperature range from 230°–300°C, preferably about 250°C. Example VII shows that the process is applicable to a mixture of DAT and MAT.

The control experiment (VIII) with terephthalic acid when compared to Experiment II shows the markedly improved yield obtained by using ammonium salts in accord with this invention.

EXAMPLE 9

Diammonium isophthalate (0.2 moles) is reacted with methanol (1.6 moles) over a basic silica gel catalyst (treated with NaOH as above) at 255°C using a contact time of 1.8 seconds to yield 59% dimethyl isophthalate after recrystallization from methanol.

EXAMPLE 10

The beneficial aspect of this process in the case of aromatic carboxylic acids derived from nitriles is shown in this example where an equilibrium hydrolyzate of TPN containing amides and ammonium salts is prepared and then, after isolation of a dry powdered hydrolyzate, the mixture is esterified to a higher yield of dimethyl terephthalate.

Terephthalonitrile (0.5 moles) is slurred in 500 ml of water and heated at 300°C for 5 minutes. The hydrolyzate, after evaporation at 100°C, is a dry powder consisting of diammonium terephthalate (29%), monoammonium terephthalate (21%), and ammonium terephthalamate (50%). The mixture (0.5 moles TPA equivalents) is reacted with methanol (4.0 moles) over an alumina catalyst containing 0.5% KOH at 255°C, contact time 1.9 seconds yielding dimethyl terephthalate (40%) and methyl terephthalamate (23%) plus unreacted hydrolysis intermediates which are recycled.

EXAMPLE 11

In a manner similar to Example 9, the diammonium salt of naphthalene-2,6-dicarboxylic acid yields dimethyl-naphthalene-2,6-dicarboxylate in good yield.

The invention claimed is:

1. A process for the preparation of a lower alkyl ester of an aromatic carboxylic acid of the benzene or naphthalene series which comprises contacting the ammonium salt of an aromatic carboxylic acid with vapors of a lower alkanol at a temperature between about 230°C., and about 300°C. in the presence of an alkaline esterification catalyst selected from the group of oxides of silicon, titanium, aluminum, zirconium and thorium, said oxides containing at least about 0.2% by weight of an alkali metal oxide.

2. The process of claim 1 where the alkanol is methanol.

3. The process of claim 2 where the ammonium carboxylic acid is diammonium isophthalate.

4. The process of claim 2 where the ammonium carboxylic acid is diammonium terephthalate.

5. The process of claim 2 where the ammonium carboxylic acid is monoammonium terephthalate.

6. The process of claim 2 where the ammonium carboxylic acid is the diammonium salt of naphthalene-2,6-dicarboxylic acid.

7. A process for the preparation of a lower alkyl ester of a phthalic acid which comprises contacting an ammonium phthalate salt obtained as a nitrile hydrolysis product with vapors of a lower alkanol at a temperature between about 230°C. and about 300°C. in the presence of an alkaline esterification catalyst selected from the group of oxides of silicon, titanium, aluminum, zirconium and thorium, said oxides containing at least about 0.2% by weight of an alkali metal oxide.

8. The process of claim 7 where the alkanol is methanol and the ammonium phthalate is derived from the hydrolysis of terephthalonitrile.

9. The process of claim 7 where the alkanol is methanol and the ammonium phthalate is derived from the hydrolysis of isophthalonitrile.

10. A process for the preparation of a lower alkyl ester of naphthalene-2,6-dicarboxylic acid which comprises contacting an ammonium salt of naphthalene-2,6-dicarboxylic acid obtained as a nitrile hydrolysis product with vapors of a lower alkanol at a temperature between about 230°C. and about 300°C. in the presence of an alkaline esterification catalyst selected from the group of oxides of silicon, titanium, aluminum, zirconium and thorium, said oxides containing at least about 0.2% by weight of an alkali metal oxide.

11. The process of claim 10 where the alkanol is methanol.

* * * * *